(12) United States Patent
Yacyshyn et al.

(10) Patent No.: US 10,433,708 B1
(45) Date of Patent: Oct. 8, 2019

(54) INDUSTRIAL OPERATION HAVING A MONITORING SYSTEM AND METHOD

(71) Applicants: Bruce Yacyshyn, Cincinnati, OH (US); Mary E. Yacyshyn, Cincinnati, OH (US)

(72) Inventors: Bruce Yacyshyn, Cincinnati, OH (US); Mary E. Yacyshyn, Cincinnati, OH (US)

( * ) Notice: Subject to any disclaimer, the term of this patent is extended or adjusted under 35 U.S.C. 154(b) by 0 days.

(21) Appl. No.: 15/638,621

(22) Filed: Jun. 30, 2017

(51) Int. Cl.
| | |
|---|---|
| *G03D 13/00* | (2006.01) |
| *A61B 1/00* | (2006.01) |
| *A61B 1/04* | (2006.01) |
| *A61B 5/06* | (2006.01) |
| *A61B 5/00* | (2006.01) |

(52) U.S. Cl.
CPC ...... *A61B 1/00016* (2013.01); *A61B 1/00029* (2013.01); *A61B 1/041* (2013.01); *A61B 1/043* (2013.01); *A61B 5/062* (2013.01); *A61B 5/0071* (2013.01); *A61B 2560/0219* (2013.01)

(58) Field of Classification Search
None
See application file for complete search history.

(56) References Cited

U.S. PATENT DOCUMENTS

| | | | | |
|---|---|---|---|---|
| 3,557,674 A | * | 1/1971 | Carney, Jr. ........... | G03B 37/005 396/19 |
| 5,754,220 A | * | 5/1998 | Smalser, Sr. ........... | G02B 23/24 348/84 |
| 5,845,033 A | | 12/1998 | Berthold et al. | |
| 6,523,554 B1 | | 2/2003 | Bryant, Sr. | |
| 6,621,516 B1 | * | 9/2003 | Wasson ............... | H04N 7/185 348/36 |
| 7,938,775 B2 | | 5/2011 | Rabinovitz et al. | |
| 8,472,795 B2 | | 6/2013 | Wang et al. | |
| 8,663,093 B2 | | 3/2014 | Rabinovitz et al. | |
| 9,505,038 B2 | | 8/2016 | Iwasaki | |
| 2004/0050394 A1 | * | 3/2004 | Jin .................... | A61B 1/00158 128/899 |
| 2004/0171915 A1 | * | 9/2004 | Glukhovsky .......... | A61B 1/041 600/160 |
| 2009/0030279 A1 | * | 1/2009 | Zander ............... | A61B 1/00036 600/118 |
| 2009/0318762 A1 | * | 12/2009 | Segawa .............. | A61B 1/00016 600/118 |
| 2010/0268025 A1 | | 10/2010 | Belson | |
| 2012/0041291 A1 | * | 2/2012 | Ferren ................. | A61B 1/041 600/365 |
| 2012/0116162 A1 | * | 5/2012 | Kawano ............. | A61B 1/00158 600/118 |
| 2016/0029998 A1 | * | 2/2016 | Brister ................ | A61B 5/6853 600/424 |

FOREIGN PATENT DOCUMENTS

JP   2007-10513   * 1/2007

* cited by examiner

*Primary Examiner* — Rodney E Fuller
(74) *Attorney, Agent, or Firm* — Mark F. Smith; Smith Brandenburg Ltd.

(57) ABSTRACT

An industrial operation having a system for remotely investigating and monitoring chemical reactions and structural and environmental conditions within the components of the industrial operation. The system includes a capsule having cameras within the capsule that operates to acquire data which is communicated to a monitor and relates to structural, environmental, chemical and/or fluid conditions within the components of the industrial operation.

9 Claims, 9 Drawing Sheets

INDUSTRIAL OPERATION HAVING A MONITORING SYSTEM AND METHOD

BACKGROUND OF THE INVENTION

The subject invention is an industrial operation having a monitoring system and method and more particularly the system and method remotely investigates and monitors industrial operations, such as chemical reactions or dispersion, or structural operations, such as conduit or pipe monitoring.

The increasing use of digital camera technology for taking and transmitting images, videos and visible information is having a major impact in industrial operations. In many industrial operations, direct human observation is not possible such as when an operation is being performed within a sealed container. Digital camera systems are highly suitable for observing and recording events within such sealed containers, such as within reactors where high, pressures and temperatures are often encountered, and can be sized to minimize their impact on the overall operation of a system. Further, such camera systems can be used for various applications including, but not limited to, recording events such as color changes, crystallization, precipitation, viscosity and other phase changes.

Various industrial operations, such as operations utilizing chemical reactions, hydrocarbon production operations, or dispersion operations, typically have one or more fluid streams that often combine or create reactions at locations having limited access but often require periodic monitoring. Accordingly, systems have been developed with sensors, such as digital cameras, that are permanently mounted at specific locations within a sealed or a limited access operation, such as an operation having one or more fluid conduits that are typically connected to a monitoring station using hard wire or wireless communication. Unfortunately, while such systems do provide the ability to monitor operations at a specific location, however sensors that fail are often expensive and difficult to reach at such locations for replacement or repair. Further, such cameras typically limited in their ability to monitor areas outside a specific defined area or a particular angle or observation direction.

Industrial operations have also been developed that utilize one or more fluid conduits, often having conduits (piping) of minimal size making it difficult to place fixed mounted cameras within the conduit. Further, such cameras often interfere with fluid streams flowing through the conduit. In many operations, the number and length of the fluid conduits are often extensive and over time blockages or damage can develop within the operation. Typically, the only indication available that a blockage or damage may have occurred or is in the process of developing is by a reduction in the flow rate of the fluid stream and/or an increase in hydrostatic head pressure. Often head pressure is the major pressure loss in an operation and when a blockage or restriction occurs it will initially have lithe effect on the flow rate within the operation since the hydraulic resistance is small relative to the much larger hydrostatic head. Thus, it may be difficult to determine if a blockage is beginning to form before it reaches the point of causing a significant reduction in fluid flow or an increase in head pressure. However, as the blockage grows, it will eventually become significant and will result in an undesirable restriction in the flow or even stop flow through the operation. Further, while the presence of blockage may be indicated, it is often difficult to determine the location of the blockage making it more difficult to repair. Therefore, it would be desirable to have an industrial operation having a system that can operate to detect impending system failure due to blockage or potential blockage of a fluid stream and allows corrective action to be implemented prior to a catastrophic event. It would also be desirable to be able to determine the extent of any damage that may have developed within a fluid conduit that could lead to a catastrophic event or before the damage expands resulting in shutdown of the industrial operation. Further, It would also be desirable to have an industrial operation having a system that can be used to observe and monitor areas within specific locations of the operation, such as where chemical reactions are occurring and where human observation is impossible or impractical and where fixed placement sensors (cameras) to not provide the necessary monitoring or where fixed cameras can cause disturbance or interfere with the fluid stream of the conduit.

Accordingly, it would be also desirable to have an industrial operation having a system that can be directed into a fluid stream to monitor conditions and reactions occurring at remote or limited access locations, that can be used to determine location of restrictions, blockages or potential blockages within a conduit, and which can be utilized to detect, identify and analyze damage or potential damage areas within an industrial operation having a fluid stream.

SUMMARY OF THE INVENTION

The subject invention is an industrial operation having a system and method for remotely investigating and monitoring components, such as chambers and conduits directing a fluid stream, of the industrial operation. The system and method operates to travel within a fluid stream and is capable of monitoring chemical reactions and structural and environmental conditions within the components of industrial operations having various chambers and/or conduits that receive and/or direct fluid streams, particularly at locations within the operation that have limited observational access. In a preferred embodiment of the invention the system comprises a capsule having one or more digital cameras within the capsule and when placed into a fluid stream of the industrial operation operates to acquire data which is communicated to a monitor and relates to structural, environmental, chemical and/or fluid conditions within the components of the industrial operation. The data captured by the one or more digital cameras is transmitted to an external receiver which is in communication with a monitor for display. In another preferred embodiment of the invention the capsule is able to travel within the fluid stream traveling through the various components of the industrial operation.

In a preferred embodiment of the invention the capsule operates to travel throughout one or more conduits and transmits image data as it travels.

In a preferred embodiment of the invention the system for remotely investigating and monitoring components includes a capsule, one or more digital cameras positioned within the capsule and a capsule processor, a battery, and a wireless transmitter unit for transmitting image data to an external receiver.

In another preferred embodiment of the invention capsule includes a light source that operates to illuminate a portion of the inner surface of a component.

In a preferred embodiment of the invention the capsule is about 9-11 mm in diameter and about 24-26 mm in length.

In a preferred embodiment of the invention the capsule, together with the devices contained within the capsule, is about 3-5 grams in weight.

In another preferred embodiment of the invention the capsule includes one or more composition sensors.

In a preferred embodiment of the invention the one or more composition sensors is selected from the list consisting of a pH sensor, a hydrogen sensor, a temperature sensor, a pressure sensor, and an electrical impedance sensor.

In another preferred embodiment of the invention the system for remotely investigating and monitoring components includes an array of antennas that cooperates with location signals and the external data processor to track the location of the capsule as it travels within a system.

In another preferred embodiment of the invention the system for remotely investigating and monitoring components includes a timer that operates to regulate the time frame and speed of obtaining image data.

In a preferred embodiment of the invention the system for remotely investigating and monitoring components includes a capsule having an attractor mechanism and component electromagnetic elements positioned along one or more point of interest locations along one or more components of the industrial operation and each operate to generate a magnetic field to direct the capsule to the point of interest location.

In a preferred embodiment of the invention the capsule includes a coil that operates to respond to the magnetic flux created by one or more electromagnets positioned along one or more components of the industrial operation to create a voltage for operating the digital camera.

Another preferred embodiment of the invention is a system for remotely investigating and monitoring components comprising one or more conduits for directing a fluid stream, the system includes a capsule having one or more sensors contained therein that operates such that when placed into a fluid stream it takes and transmits data related to a chemical reaction within the fluid stream.

In a preferred embodiment of the invention the transmitted data relates to environmental conditions within the component and includes image data.

In a preferred embodiment of the invention the chemical reaction is a dispersal process of chemical agents.

In a preferred embodiment of the invention the chemical agents are cleaning agents.

In a preferred embodiment of the invention the chemical reaction is a coagulation process.

In a preferred embodiment of the invention the chemical reaction is a clogging or blockage process that effects the functioning of the industrial operation.

In a preferred embodiment of the invention the chemical reaction is a redox process taking place along the inner surface of a component of the industrial operation.

In a preferred embodiment of the invention the chemical reaction is a corrosion process taking place along the inner surface of a component of the industrial operation.

In another preferred embodiment of the invention the system operates to identify areas of damage at one or more locations within one or more components of the industrial operation.

Other advantages, objects, and embodiments of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which.

DETAILED DESCRIPTION OF THE INVENTION

The subject is an industrial operation having a system and method for remotely investigating and monitoring chemical, environmental and structural systems. In a preferred embodiment of the invention the industrial operation the system comprises a capsule and a digital camera apparatus contained within the capsule such that when placed into a fluid stream it operates to transmit image data related to chemical operations and/or conditions at a location. Data captured by the digital camera apparatus is transmitted by a transmitter unit to an external receiver in communication with a processor that operates to display image data on a monitor. In a preferred embodiment of the invention the capsule is able to travel freely (without wires, cable and the like extending outwardly from the industrial operation) within components of the industrial operation for obtaining data.

Figure 1:
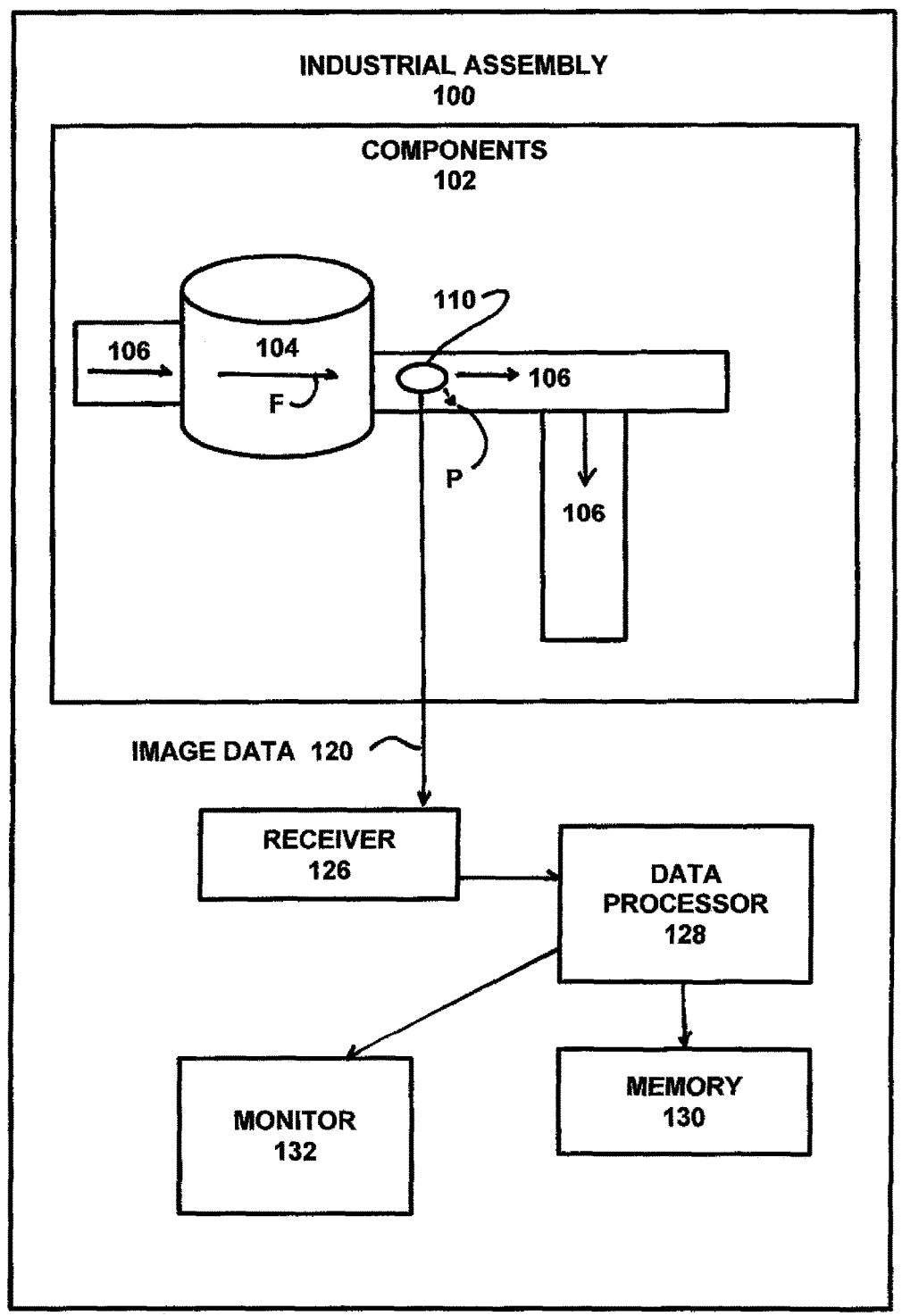
FIG. 1 is a schematic illustration of an industrial operation having one or more components, such as one or more chambers and one or more conduits, that utilize and direct fluid flow and showing a capsule contained therein for traveling within the flow to remotely investigate and monitor conditions within the one or more components.
Figure 2:
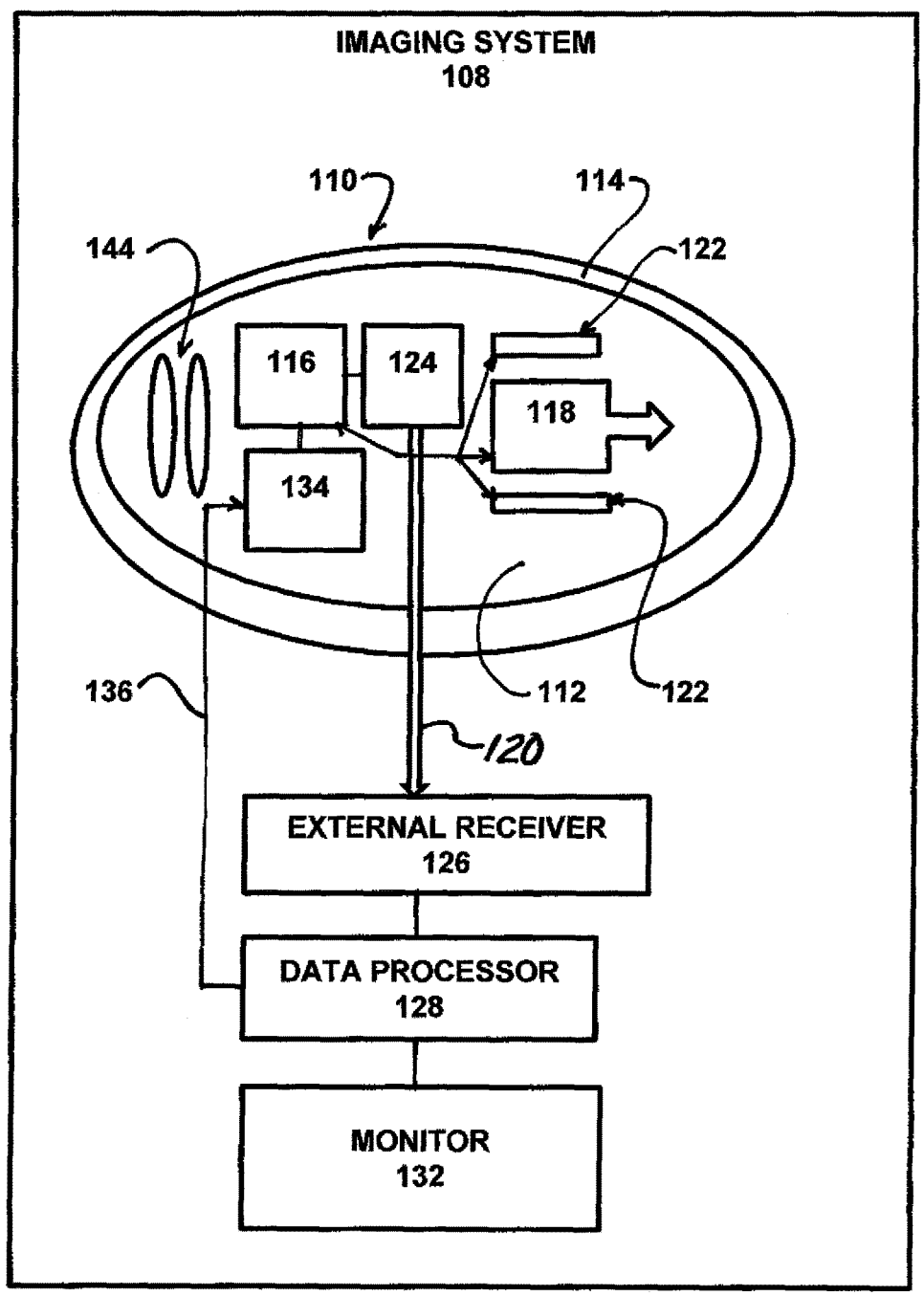
FIG. 2 is a schematic illustration showing the imaging system for remotely investigating and monitoring industrial operation of FIG. 1 wherein the capsule contains a capsule processor, a command receiver, one or more digital cameras for capturing image data, a transmitter unit for transmitting image data, an external receiver for receiving the transmitted image data, a processor and a monitor for displaying the image data.

Referring to FIGS. 1 and 2, a preferred embodiment of an industrial operation 100 is shown having one or more components 102. In a preferred embodiment the one or more components 102 include at least one chamber 104 and one or more conduits 106 for directing a flow of constituents F through the industrial operation 100. It should be understood that the flow of constituents can be in the form of fluid flow, such as liquid or gas flow, or can be in the form of particles, such as powders or other similar forms, that can be directed through one or more conduits. The industrial operation 100 further includes a system, in the form of an imaging system 108, for remotely investigating and monitoring structural, environmental, and/or reactions within the components of the industrial operation 100 and comprises a capsule 110 sized for effectively inserting into the one or more components 102.

As shown, the capsule 110 has an elongated shape, such as, but not limited to an oblong, oval, spherical, tubular cross-section, and includes an inner cavity 112 and has a transparent or semi-transparent casing portion 114 or windows. Positioned within the inner cavity 112 is a capsule processor 116, one or more digital cameras 118 that operate to take image data 120 through the transparent casing portion 114, a light source 122 which operates to provide illumination within an inner portion P of a component 102, a transmitter unit 124 for transmitting the image data 120 to an external receiver 126, such as by way of Radio Frequency (RF) signals or other types of communication signals The external receiver 126 operates in communication with an external data processor 128 and memory 130 that cooperate with a monitor 132 to record and display the image data 120. In a preferred embodiment of the invention, the inner cavity 112 of the capsule 110 further includes a command receiver 134 that operates to receive command signals 136 providing instructions from the external data processor 128 and is in communication with the capsule processor 116 for implementing the instructions. Preferably, in order to enter into relative small chambers 104 and conduits 106 comprising the one or more components 102 with minimal disruption to the operation of the industrial operation 100, the capsule 110 is minimal in size while being able to be inserted into the one or more components 102 and flow through the various components 102 for taking and transmitting image data 120. Preferably, the capsule 110 is about 9-11 mm in diameter and about 24-26 mm in length. In addition, the capsule 110 should be light in weight enough to easily travel freely with the flow of constituents F of the industrial operation 100. Preferably, the capsule should weigh between about 3-5 grams. One such capsule having a digital camera for taking and transmitting image data and sized such that it is capable of traveling freely with the flow of components of an industrial operation is manufactured by Given Imaging Ltd. of Israel and distributed by Ethicon Endo-Surgery under the mark PILLCAM. Other such systems are show and described in U.S. Pat. Nos. 8,663,093, 7,938,775 which are incorporated herein in their entirety.

Figure 3:
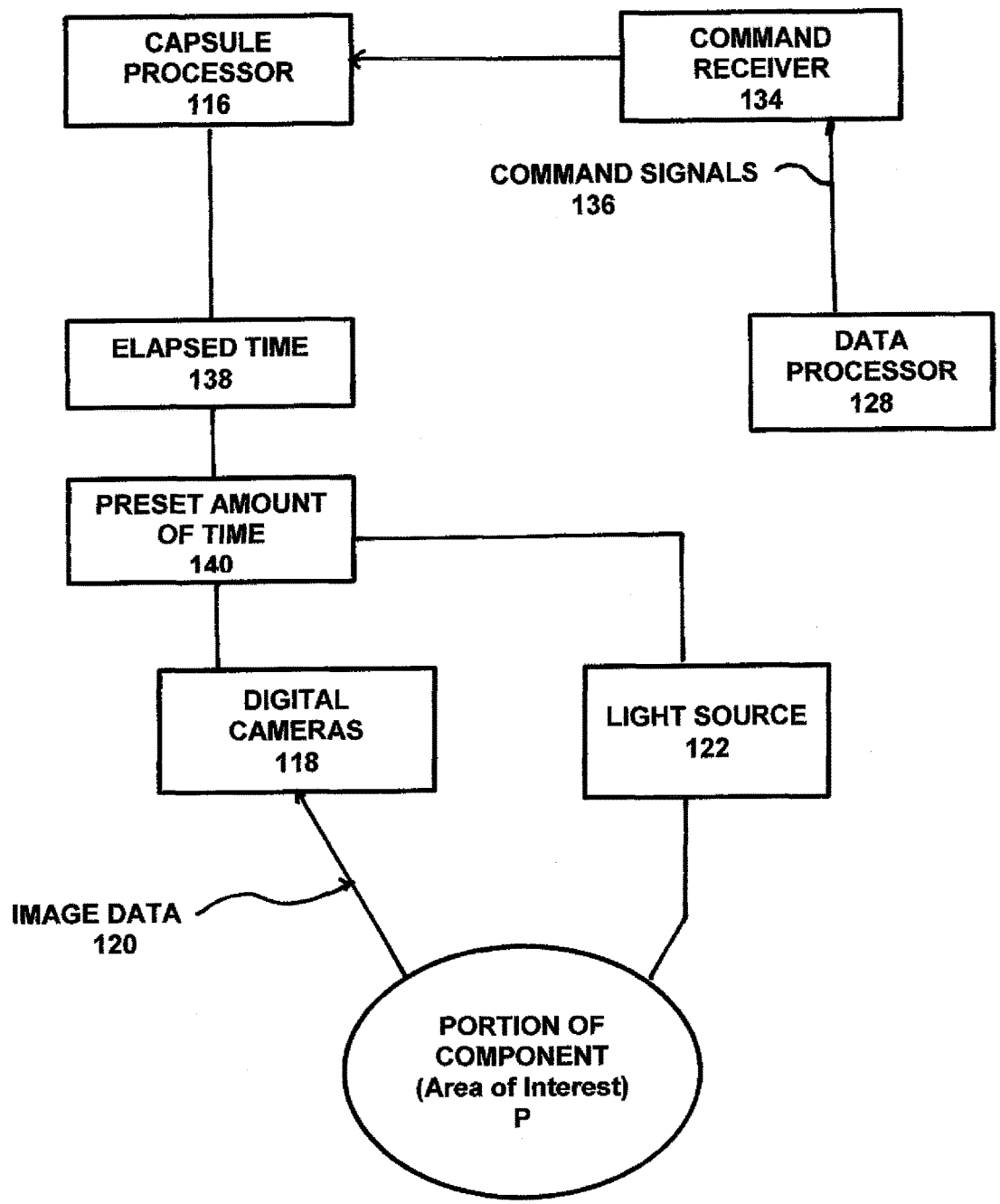
FIG. 3 is a schematic illustration showing the system for remotely investigating and monitoring industrial operations of FIG. 1 wherein the capsule processor operates to track elapsed time and when a preset amount of elapsed time is reached, the capsule processor activates a light source and the one or more digital cameras to capture image data of a portion of a component.

It should be understood that that the one or more digital cameras 118 can operate to capture image data 120 such as in the form of still images or video images. In a preferred embodiment of the invention the one or more digital cameras 118 are in the form of a charge coupled device (CCD) camera apparatus. It should be understood that the one or more digital cameras can include different lenses depending on the purpose or type of image data required and/or the size of the various components. For example, the lenses can include far field lenses, close-up lenses, narrow focus lenses, or wide angle (fish eye) lenses. Preferably the light source 122 is an incandescent, fluorescent, chemiluminescent, laser diode or a light emitting diode (LED) light source that operates to direct light to an inner portion P of one or more components 102 sufficient to permit the one or more digital cameras 118 to capture image data 120. In a preferred embodiment of the invention the capsule processor 116 is in electrical communication with the light source 122 and the one or more digital cameras 118 such that the light source 122 is activated to provide illumination within a portion P of a component 102 when the one or more digital cameras 118 operate to take image data 120, such as in the form of an image or a video, of the portion P. In this way power is conserved thereby increasing the maximum operation time of the imagining system 108. In another preferred embodiment of the invention the capsule processor 116 further functions to control the intensity of the light being radiated by the light source 122 thereby increasing the operation time of the imaging system 108. In another preferred embodiment of the invention the capsule processor 116 is in electrical communication with the one or more digital cameras 118 and operates to control the frequency by which the one or more digital cameras 118 acquires image data 120. In another preferred embodiment of the invention, as illustrated in FIG. 3, the capsule processor 116 operates as a counter (or connected to a timing circuit) that measures elapsed time 138 and after a preset amount of time 140 activates the light source 122 and the one of more digital cameras 118 to acquire image data 120. It should be understood that the capsule processor 116 can also operate to deactivate the light source 122 and the one or more digital cameras 118 after a preset amount of image data 120 (i.e. number of images or video frames) has been taken or after a certain amount of time has passed. In another preferred embodiment of the invention the capsule processor 116 can be in communication with the external data processor 128, such as through a transmitter within the data processor and an external transmitter that operates to transmit the command signals from the data processor (not shown), through the command receiver 134 that operates to direct command signals 136 to the capsule processor 116 which operates to control the operation of the light source 122 and the one or more digital cameras 118 to take image data 120.

Figure 4:
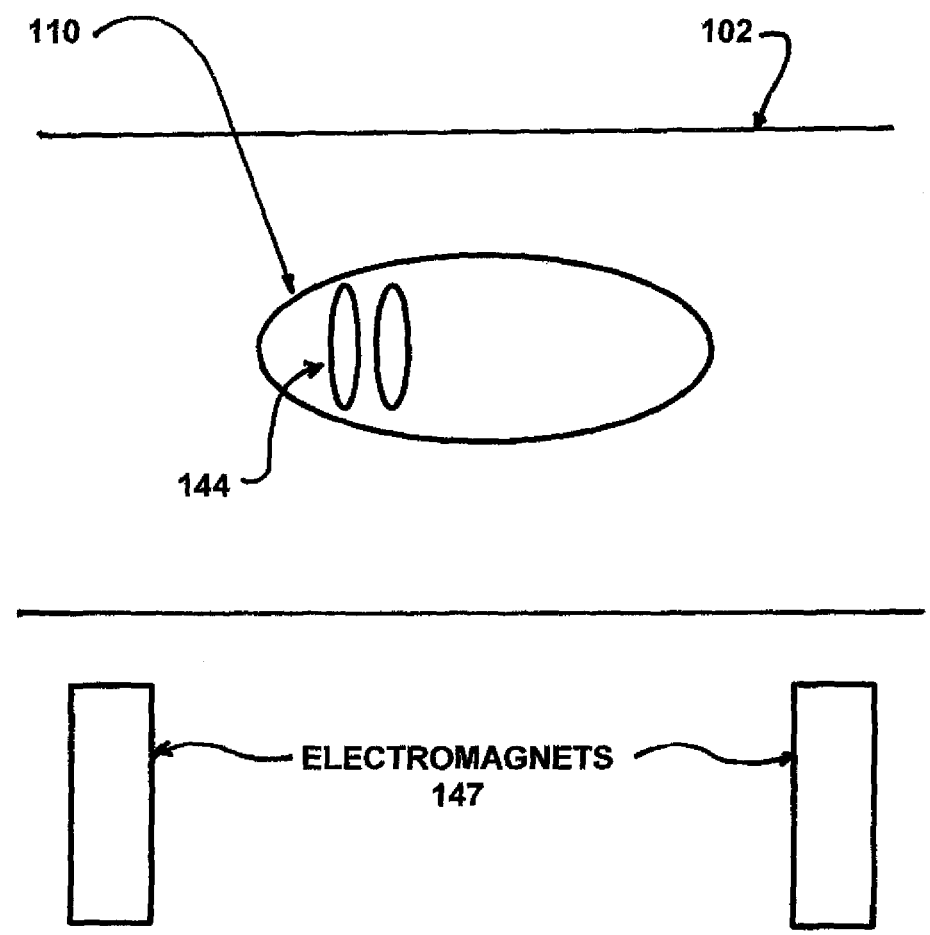
FIG. 4 is a schematic illustration showing the system for remotely investigating and monitoring industrial operations of FIG. 1 further comprising a power source in the form of batteries or using induction coils for providing electrical power to operate the components within the capsule.

In a preferred embodiment of the invention as illustrated in FIG. 2, positioned within the cavity 112 of the capsule 110 is a power source 144 that provides electrical power to operate the one or more digital cameras 118, the light source 122 and the transmitter unit 124 to transmit image data 120 to the external receiver 126 and the external data processor 128. Preferably the power source 144 is in the form of one or more batteries, such as one or more silver oxide batteries, lithium batteries or other suitable electrochemical cells. In another preferred embodiment of the invention, as illustrated in FIG. 4, the power source 144 is in the form of convention wireless power source such as inductive system whereby a wire coil 145 within the capsule 110 operates to respond to the magnetic flux created by one or more electromagnets 147 positioned along one or more components 102 of the industrial operation 100 to create a voltage for operating the one or more digital cameras 118. Such systems are shown and described in U.S. Patent Application No. 2005/0064815 and U.S. Patent Application No. 2005/228259 and U.S. Patent Application No. 2007/065407 which are incorporated herein in their entirety. Other systems, such as resonant inductive coupling system in which power is transferred by magnetic fields between two resonant circuits (one in the external transmitter and one contained within the capsule) that operate to transfer electric power to the electrical components contained within the capsule may also be used.

Figure 5:
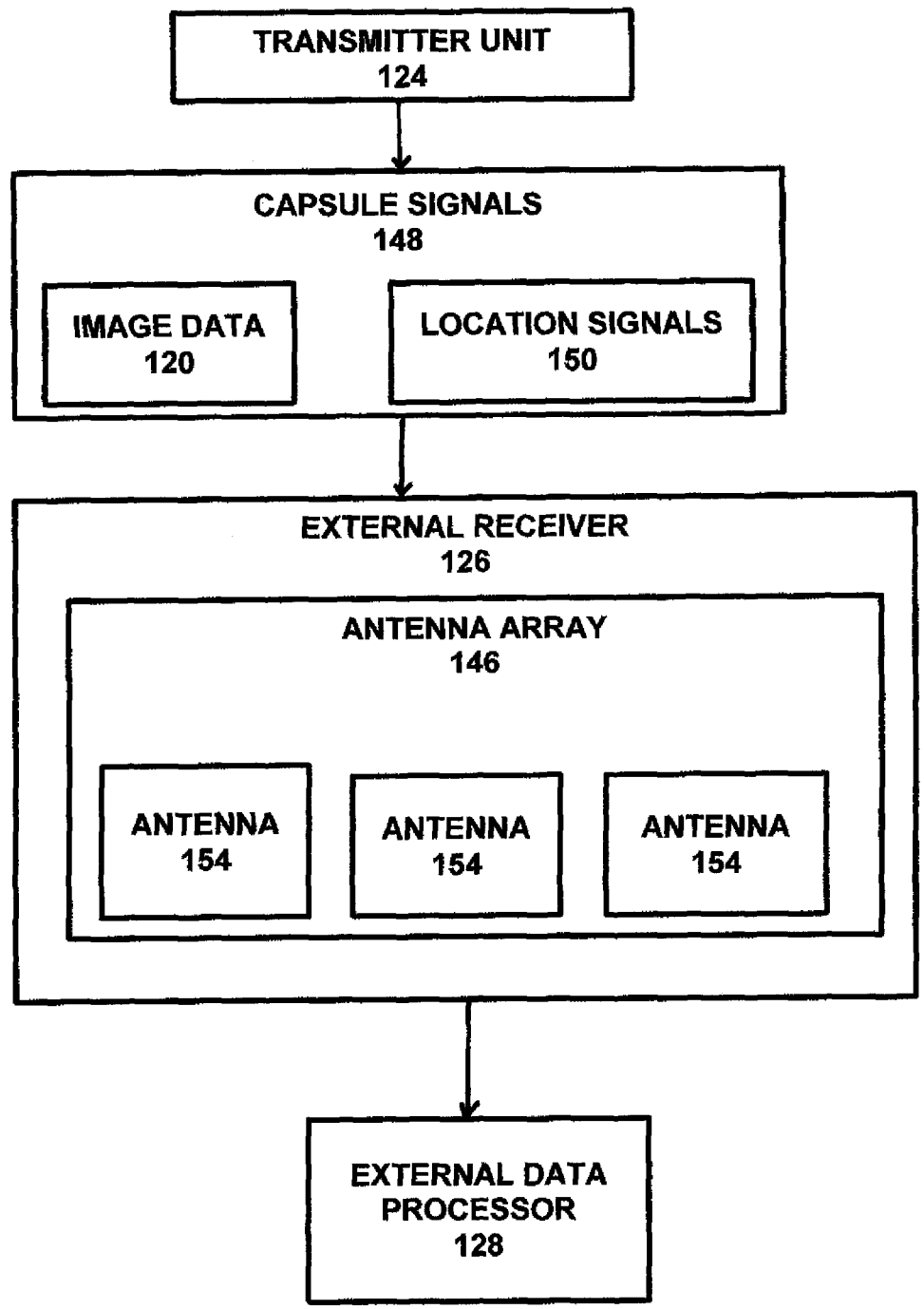
FIG. 5 is a schematic illustration showing the system for remotely investigating and monitoring industrial operations of FIG. 1 showing the transmitter unit within the capsule transmitting capsule signals, such as image data and location signals, to an external receiver having an antenna array positioned along the external surface of the one or more components for receiving the capsule signals and transmitting them to the external data processor.

In another preferred embodiment of the invention, as illustrated in FIG. 5, the external receiver 126 of the imaging system 108 includes an array of antennas 146 positioned externally along the one or more components 102 that operate to receive capsule signals 148 being transmitted by the transmitter unit 124. In a preferred embodiment of the invention the capsule signals 148 include image data 120 and location signals 150. The array of antennas 146 operate to receive such capsule signals 148 and directs them to the external data processor 128. In another preferred embodiment of the invention the transmitter unit 124, command receiver 134, the external receiver 126 and the processor operate using a BLUETOOTH system that operates to receive and transmit signals, such as the image data and command signals, between the transmitter unit, the command receiver, the external receiver 126 and the external data processor 128 having a transmitter therein. It should be understood that the array of antennas 146 are positioned externally along the one or more components 102, particularly along the outside of a component where the inner portion P is of concern. It should also be understood that the number of antennas and the position of the antennas is determined by the size of the components, the material forming the components and the signal strength.

The external data processor 128 together with location signals 150 being transmitted by the transmitter unit 124 and received by the array of antennas 146 operates to calculate the positional coordinates of the capsule 110 within the one or more components 102. In a preferred embodiment of the invention the external data processor 128 calculates the transmission time that it took for the location signal 150 to be transmitted by the transmitter unit 124 and received by a particular antenna of the array of antennas 146. The total transmission time together with the direction of the particular antenna allows the external data processor 128 to precisely determine the capsule's position within the one or more components 102. Accordingly, by measuring the transmission time of the location signals 150 and the strength of reception by each antenna of the array of antennas 146 allows the external data processor 128 to derive the precise location of the capsule 110 within the one or more components 102. It should now be understood that by actively receiving signals the movement of the capsule can be continuously tracked within the one or more components 102.

Preferably, the array of antennas 146 comprises at least three antennas 154 for determining the location of the capsule within the one or more components. However, depending on the size and design of the industrial operation additional antennas can be used to increase the accuracy of the measured location of the capsule 110. Location signals 150 being send by the transmitter unit 124 received by the array of antennas 146 and transmitted to the external data processor 128 are measured for their signal strength received by each antenna 154 and the signal time received by each antenna 154 and the external data processor 128 using conventional triangular technique operates to precisely determine the capsule's position within the one or more components 102.

Preferably, the array of antennas 146 cooperate with the external data processor 128 for determining the location of the capsule 110 within the one or more components 102, such as through the use of triangulation and received location signals 150 being transmitted by the transmitter unit 124. However, it should be understood that other position tracking systems can be utilized for determining the position of the capsule 110 within the one or more components 102 including using energy levels within the location signals 150, or by using timing and the flow velocity of the constituents F traveling through the one or more components 102.

Figure 6:
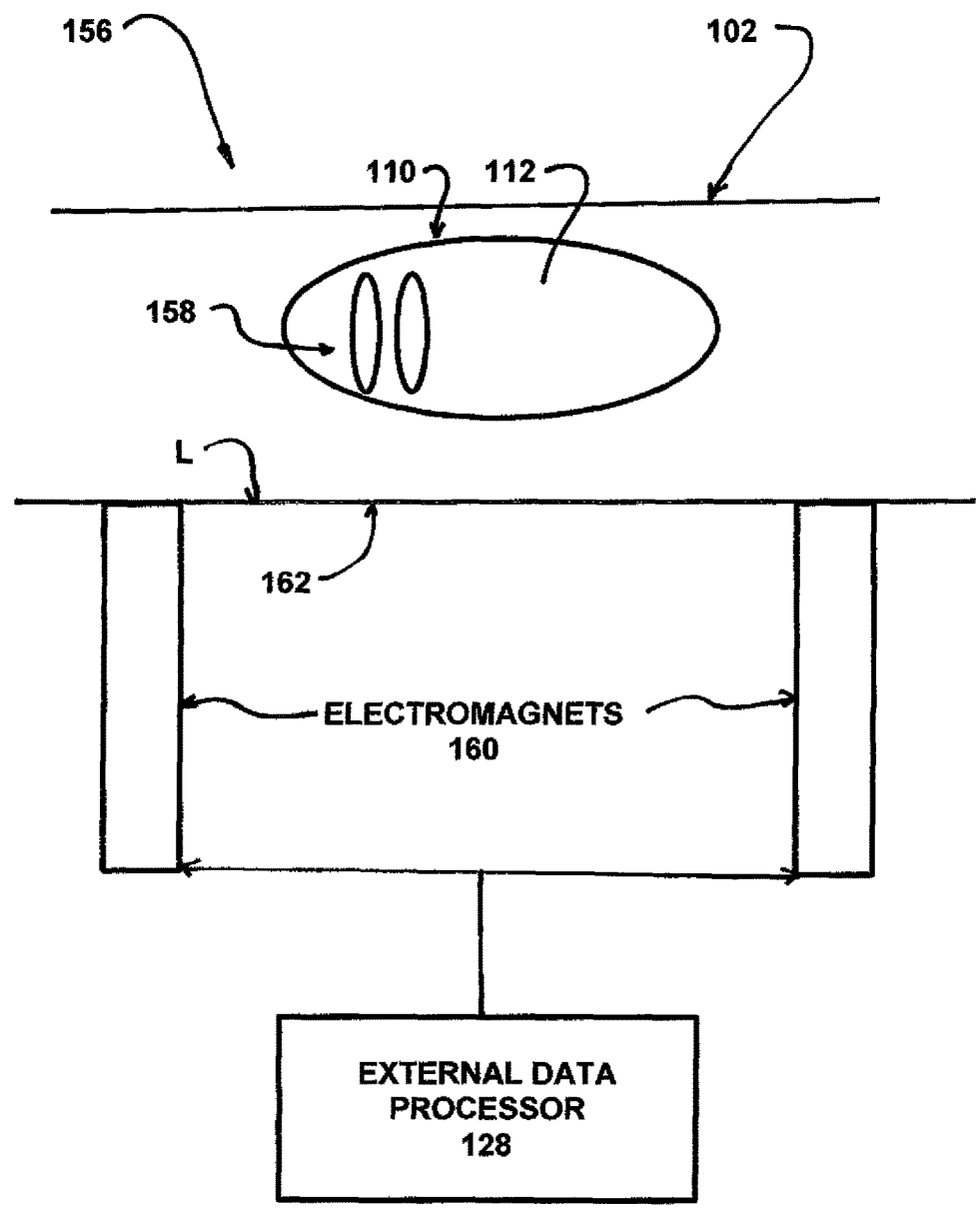
FIG. 6 is a schematic illustration showing the system for remotely investigating and monitoring industrial operations of FIG. 1 wherein the capsule includes an attractor mechanism that cooperates with component electromagnetic elements to direct the capsule to a specific location within the one or more components.

In another preferred embodiment of the invention, as illustrated in FIG. 6, the imaging system 108 further includes a capsule positional system 156 having an attractor mechanism 158, in the form of one or more capsule magnets or ferritic material or other magnetically attracted material, positioned within the inner cavity 112 of the capsule 110 that cooperate with one or more component electromagnetic elements 160 positioned along the external surface 162 of the one or more components 102. The electromagnetic elements 160 are in communication with the external data processor 128 that functions to direct electrical current to activate and deactivate the individual electromagnetic elements 160. In operation, as the capsule 110 travels internally through the one or more components 102 the attractor mechanism 158 cooperates with an activated component electromagnetic element 160 to direct the capsule 110 to an internal location L within the one or more components 102 closest to the activated component electromagnetic element 160 which together operates to retain and hold the capsule 110 in position at the internal location L for a desired length of time (until the component electromagnetic element is deactivated). It should be understood that the capsule 110 can be maintained at that location L until a desired amount of image data 120 has been collected and transmitted by the transmitter unit 124 to the external receiver 126. It should be understood that by placing the component electromagnetic elements 160 in various positions along the external surface of the one or more components, the capsule can be directed to different parts of the industrial operation 100 to capture image data as needed.

Figure 7:
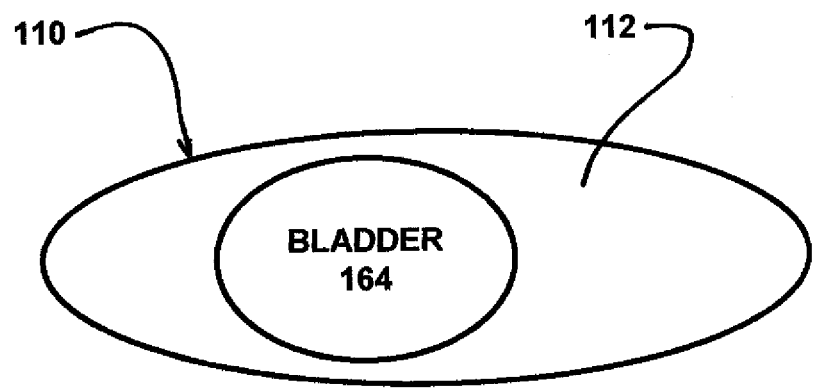
FIG. 7 is a schematic illustration showing the system for remotely investigating and monitoring industrial operations of FIG. 1 wherein the capsule includes a bladder or other materials that provide the desired amount of buoyancy to the capsule to permit the capsule to freely move within the flow of constituents.

In another preferred embodiment of the invention, as shown in FIG. 7, the inner cavity 112 of the capsule 110 includes a bladder 164 that can be filled with different materials having different densities for providing weight to the capsule 110. For a non-limiting illustration, the capsule can be weighted to provide the desired buoyancy for traveling in the flow of constituents through the one or more components. In some cases, it may be desirable for the capsule to travel near the top of the flow near the top of the internal surfaces of the one or more components. In other cases, it may be desirable for the capsule to travel near the bottom of the internal surfaces of the one or more components or travel through the middle of the flow.

Figure 8:
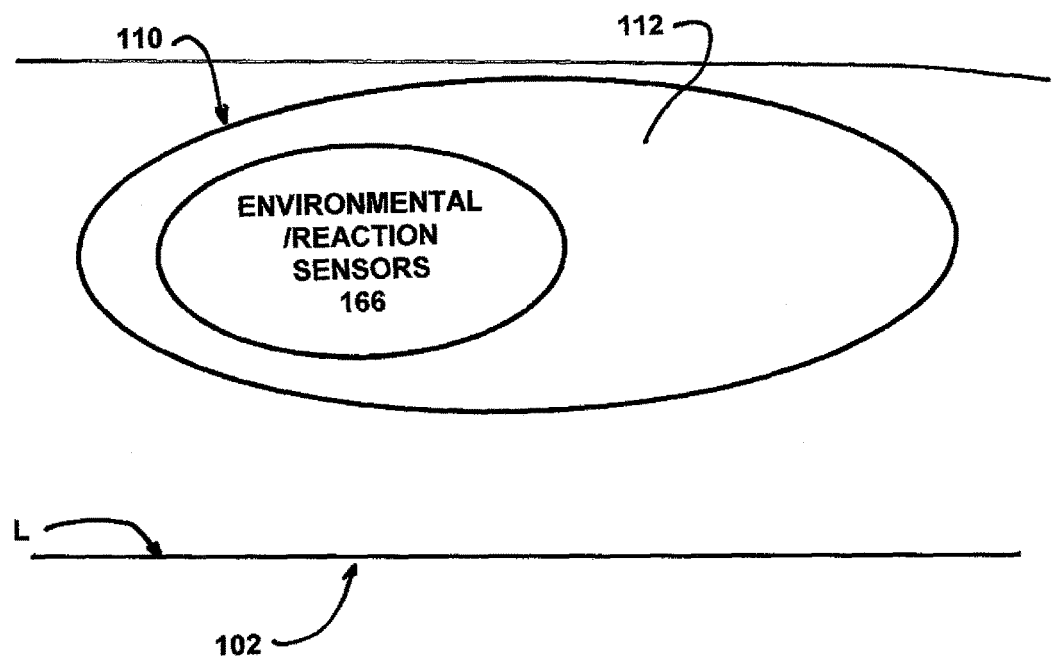
FIG. 8 is a schematic illustration showing the system for remotely investigating and monitoring industrial operations of FIG. 1 wherein the capsule includes one or more environmental/reaction sensors for measuring one or more environmental conditions within the one or more components or for providing data of a reaction taking place at a location within the one or more components.

In another preferred embodiment of the invention, as illustrated in FIGS. 1 and 8, the capsule 110 includes one or more environmental/reaction sensors 166 that operate to provide information concerning the environment or reactions occurring at a location L within the one or more components 102 of the industrial operation 100. Preferably, the one or more environmental/reaction sensors 166 are selected from the list consisting of a pH sensor, a hydrogen sensor, a temperature sensor, a pressure sensor, and an electrical impedance sensor.

Figure 9:
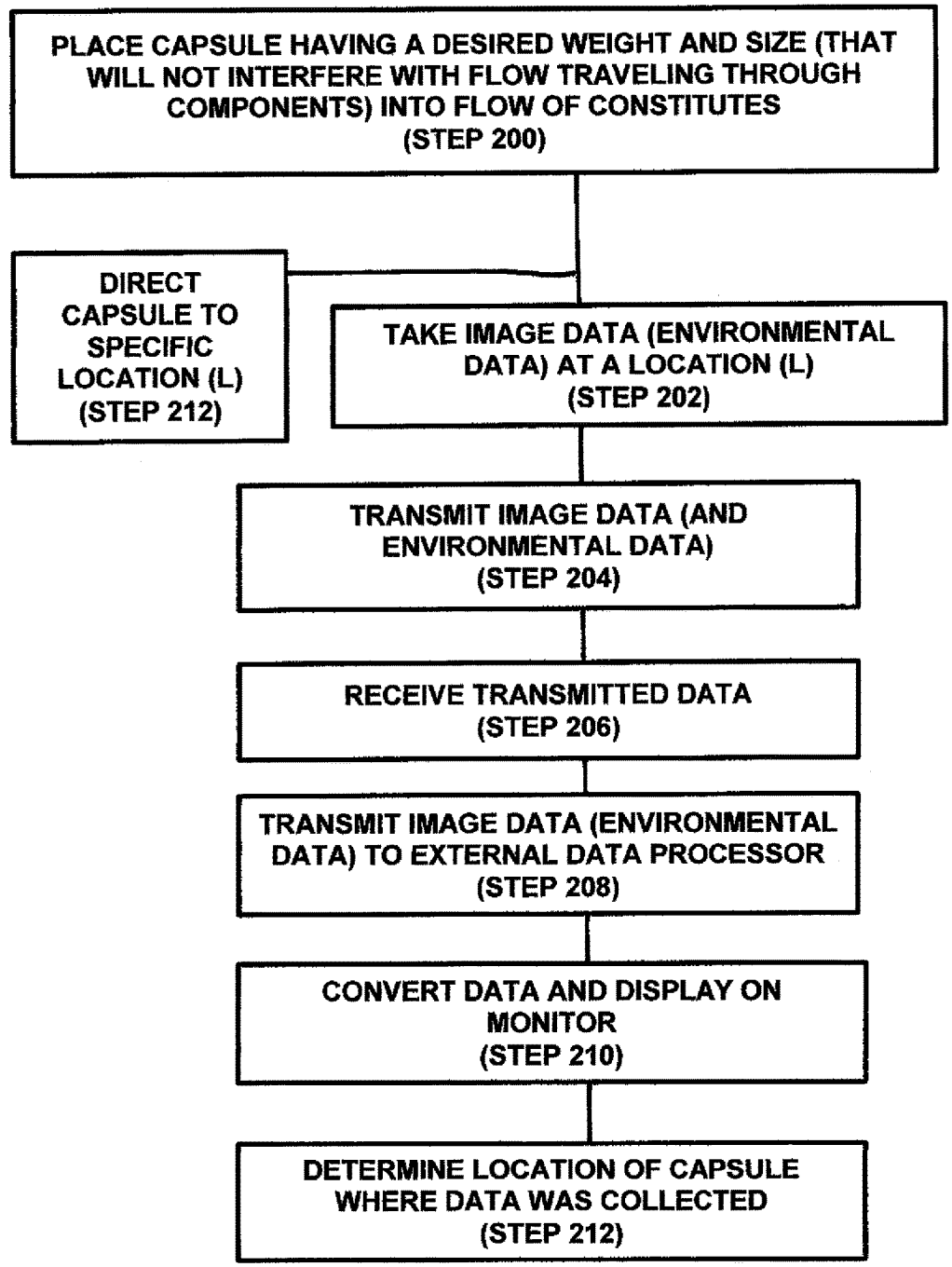
FIG. 9 is a schematic flow chart illustration the steps for obtaining image and/or environmental/reaction data within one or more components of an industrial operation.

In operation, as illustrated FIG. 9, an industrial operation is shown having one or more components and a flow of constitutes traveling through the interior of the one or more components. The industrial operation includes a system for investigating and monitoring process within the one or more components and includes a capsule having an imaging system. The capsule includes an inner cavity having one or mire digital cameras therein and is of a desired weight and size so that it does not disrupt the flow of constitutes such that it interferes or causes a disruption with the industrial operation when placed into the flow of constitutes through an inlet (step 200). The capsule travels through the fluid stream and, operates to take image data (or in a preferred embodiment environmental data) of an inner portions of the one or more components (step 202). Preferably the image data is of a process selected from the list consisting of a cleaning process, a dispersal process, a dissolving process, a clogging process, a redox process and a corrosion process, or of a blockage or damage at, a location within the one or more components. The image data is transmitted by a transmitter unit contained within the capsule (step 204) and the image data is received by an array of antennas (step 206) which then transmits the image data to an external data processor (step 208) which functions to convert the image data and display it on a monitor (step 210). Preferably, the capsule location is determined (step 212) and the portion of the one or more components is associated with the image data. In a preferred embodiment of the invention data is also taken and transmitted to the external data processor which includes data as to the environmental conditions or reactions taking place at a Location within the one or more components at the location. In another preferred embodiment of the invention the imaging system is provided with a capsule positioning system and the capsule is directed to specific locations within the one or more components (step 212) where image data and/or environmental data is collected and transmitted for viewing by an external monitor.

Is should now be apparent that the subject invention is an industrial operation having a system and method for remotely investigating and monitoring components, such as chambers and conduits directing a fluid stream, of the industrial operation. The system and method for remotely investigating and monitoring components of an industrial operation. Such industrial operations can include operations having a fluid stream whereby the system includes the monitoring system described above that is capable of monitoring chemical reactions and structural and environmental conditions particularly at locations within the operation that have limited observational access. It should be apparent that the invention covers various industrial operations utilizing the system and method for remotely investigating and monitoring components. In a non-limiting illustration the industrial operation can include hydrocarbon production and the system for monitoring can be used to provide pressure gradients in the hydrocarbon production flow-line. In another non-limiting illustration the system and method for remotely investigating and monitoring components can be utilized to observe (take images) and to capture environmental conditions within one or more components of the industrial operation where chemical reactions are taking place. Such chemical reactions can be part of the industrial operation or may be reactions, such as deterioration of a component within a component of the industrial operation. Accordingly, the monitoring system provides the ability to detect deterioration and the level of deterioration. In another non-limiting illustration the industrial operation includes a system for remotely investigating and monitoring components that provides the ability to determine if resistance is developing, such as the formation of blockage, within one or more of the components that if permitted to grow will impede or block the flow of constituents traveling through the components. Accordingly, the system operates to determine the location of any such resistance prior to the resistance growing in severity until it becomes significant and results in an undesirable restriction in the flow or even stop flow through the operation. Further, the system operates to provide location of the blockage.

It should be understood that the monitoring system of the industrial operation can be utilized to collect various data (image data, environmental data and reaction data) within a flow of constituents within the one or more components of an industrial operation. For non-limiting examples, the imaging system can be used to obtain data on a dispersal process of chemical agents, such as but not limited to cleaning agents, or on coagulation processes, or a dissolving process, or on clogging or blockage process that effects the functioning of the industrial operation. In another illustration the industrial operation includes processes, such as the dissolving or materials (i.e. how fast and/or how effective a material is dissolving within a fluid). For a non-limiting example, the system and method of the subject invention can be used for monitoring and observing a tablet or chemical dissolution in an industrial (or household appliance) operation agitation device. Accordingly, depending on the dissolution performance environmental conditions can be adjusted (such as adding or subtracting chemical agents into the fluid stream to adjust the pH of the fluid stream or at the location of the component (in the agitator for example)). In industrial operations utilizing pharmaceutical agents (such as but not limited to tablets, suppository or other physical forms of an administered drug), the system and method of the subject invention can operate to monitor and/or observe how the administrative drug dissolves in states of agitation or non-agitation (no peristalsis) systems. The system and method further can operate to acquire data and information of industrial operations, such as but not limited to pharmaceutical operations, allowing comparisons to be made of dissolution and dispersal characteristics of competing or similar drug products to show similarity or non-similarity of products.

Further, the imaging system can be used to obtain data on redox processes or corrosion processes taking place along the inner surface of a component of the industrial operation. Further, the imaging system can provide data and identify areas of damage or potential areas of concern at one or more locations within one or more components of the industrial operation.

Therefore, it should also now be apparent that the industrial operation includes a system that operates to detect impending system failure due to blockage or potential blockage of a fluid stream and allows corrective action to be implemented prior to a catastrophic event. Further, the system operates to determine the extent of any damage that may have developed within a fluid conduit that could lead to a catastrophic event or before the damage expands resulting in shutdown of the industrial operation. Accordingly, the subject invention is an industrial operation having a system that can be directed into a fluid stream to monitor conditions and reactions occurring at remote or limited access locations, that can be used to determine location of restrictions, blockages or potential blockages within a conduit, and which can be utilized to detect, identify and analyze damage or potential damage areas within an industrial operation having a fluid stream.

The invention claimed is:

1. A method for remotely investigating and monitoring chemical reactions comprising the steps of:
    placing a capsule having a weight and size into the fluid stream of an industrial operation having one or more components having at least one chamber and one or more conduits that operate to direct a fluid stream through the industrial operation, wherein the weight and size of the capsule does not interfere with the fluid stream to cause interference with the operation of the industrial operation;
    directing the capsule to a specific location within the one or more components;
    taking image data of a chemical reaction at the specific location within the one or more components using an imaging system contained with the capsule;
    using one or more environmental/reaction sensors within the capsule to obtain environmental and reaction information at the specific location within the one or more components; and
    transmitting the image data and information to an external data processor and viewing the image data and information on a monitor.

2. The method of claim 1 wherein the chemical reaction is selected from the list consisting of a cleaning process, a dispersal process, a dissolving process, a clogging process, a redox process and a corrosion process.

3. The method of claim 1 further comprising the step of monitoring the location of the capsule.

4. The method of claim 1 wherein said capsule further includes a light source that operates to illuminate a portion of an inner surface of a component.

5. The method of claim 1 wherein said one or more environmental/reaction sensors is selected from the list consisting of a pH sensor, a hydrogen sensor, a temperature sensor, a pressure sensor, and an electrical impedance sensor.

6. The method of claim 1 wherein the system further comprises the step of using an array of antennas that cooperates with location signals and an external data processor to track the location of the capsule as it travels within the one or more components.

7. The method of claim 1 further comprising the step of using an attractor mechanism and one or more component electromagnetic elements positioned at locations along the outer surfaces of the one or more components and each component electromagnetic element operates to generate a magnetic field that functions to direct the capsule to the specific location within the industrial operation.

8. The method of claim 1 further comprising the step of using a timer that operates to regulate time frame and speed of a camera that operates to take image data.

9. The method of claim 1 further comprising the step of using magnetic flux created by one or more electromagnets positioned along the one or more components to create a voltage for operating a digital cameral positioned within the capsule.

* * * * *